United States Patent
Legrand et al.

(10) Patent No.: US 8,257,447 B2
(45) Date of Patent: Sep. 4, 2012

(54) COMPOSITION COMPRISING AN ALKANOLAMINE, AN AMINO ACID AND A CATIONIC POLYMER

(75) Inventors: Frédéric Legrand, Westfield, NJ (US); Jean-Marc Ascione, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/808,585

(22) PCT Filed: Dec. 17, 2008

(86) PCT No.: PCT/EP2008/067786
§ 371 (c)(1),
(2), (4) Date: Feb. 22, 2011

(87) PCT Pub. No.: WO2009/080668
PCT Pub. Date: Jul. 2, 2009

(65) Prior Publication Data
US 2011/0138545 A1    Jun. 16, 2011

Related U.S. Application Data

(60) Provisional application No. 61/006,539, filed on Jan. 18, 2008.

(30) Foreign Application Priority Data

Dec. 20, 2007  (FR) ...................... 0760135

(51) Int. Cl.
*A61Q 5/10* (2006.01)
(52) U.S. Cl. ............. 8/405; 8/406; 8/431; 8/435; 8/455; 8/547; 8/552; 8/604; 8/606

(58) Field of Classification Search ............. 8/405, 406, 8/431, 435, 455, 547, 552, 604, 606
See application file for complete search history.

(56) References Cited

U.S. PATENT DOCUMENTS

| | | | |
|---|---|---|---|
| 6,540,791 B1 * | 4/2003 | Dias | 8/111 |
| 7,458,993 B2 | 12/2008 | Cottard et al. | |
| 2004/0231068 A1 | 11/2004 | Cotteret et al. | |
| 2004/0237218 A1 * | 12/2004 | Marsh et al. | 8/405 |
| 2005/0188480 A1 * | 9/2005 | Lim et al. | 8/405 |

FOREIGN PATENT DOCUMENTS

| | | |
|---|---|---|
| DE | 10 2006 033 074 A1 | 5/2007 |
| DE | 10 2005 059 647 A1 | 6/2007 |
| EP | 1 374 842 A1 | 1/2004 |
| EP | 1 428 511 A1 | 6/2004 |
| JP | 59-106413 | 6/1984 |
| JP | 2004-262885 | 9/2004 |
| JP | 2004-262886 | 9/2004 |
| WO | WO 97/04739 | 2/1997 |

OTHER PUBLICATIONS

French Search Report for FR 0760135 dated Aug. 19, 2008.
English language abstract of DE 10 2005 059 647 A1, Jun. 14, 2007.
English language abstract of DE 10 2006 033 074 A1, May 16, 2007.
English language abstract of JP 59-106413, Jun. 20, 1984.
English language abstract of JP 2004-262885, Sep. 24, 2004.
English language abstract of JP 2004-262886, Sep. 24, 2004.

* cited by examiner

*Primary Examiner* — Eisa Elhilo
(74) *Attorney, Agent, or Firm* — O'Brien Jones PLLC

(57) ABSTRACT

Compositions for treating keratin fibers comprising, in a cosmetically acceptable medium, at least one alkanolamine, at least one amino acid, and at least one cationic polymer. Also provided are methods of bleaching and/or coloring keratin fibers and multiple-compartment devices or kits for the implementation of these methods.

22 Claims, No Drawings

COMPOSITION COMPRISING AN ALKANOLAMINE, AN AMINO ACID AND A CATIONIC POLYMER

CROSS REFERENCE TO RELATED APPLICATIONS

This application is a national phase application based on PCT/EP2008/067786, filed Dec. 17, 2008, which claims the priority of French Patent Application No. 0760135, filed Dec. 20, 2007, and claims the benefit of U.S. Provisional Application No. 61/006,539, filed Jan. 18, 2008, the content of all of which is incorporated herein by reference.

The present invention provides a composition for treating keratin fibres, and especially human keratin fibres such as the hair, which comprises, in a cosmetically acceptable medium, one or more alkanolamines, one or more amino acids and one or more cationic polymers.

It is known practice, for the treatment of hair, to use oxidizing compositions, more particularly for dyeing human keratin fibres, and especially the hair, with dyeing compositions containing oxidation dye precursors, generally referred to as oxidation bases. These oxidation bases are colourless or weakly coloured compounds which, in combination with oxidizing products, give rise, by a process of oxidative condensation, to coloured compounds.

The method of oxidation dyeing involves applying, to the keratin fibres, oxidation bases, or a mixture of oxidation bases and couplers, with an oxidizing agent, such as hydrogen peroxide, which is added at the time of use.

Generally speaking, this method is implemented at an alkaline pH, more particularly in the presence of ammonia, and produces a dyeing and, at the same time, a lightening of the fibre that is manifested in practice by the possibility of obtaining an eventual coloration which is lighter than the original colour. Moreover, the lightening of the fibre has the advantageous effect of bringing about a unified colour in the case of depigmented hair, and of emphasizing the colour—that is, making it more visible—in the case of naturally pigmented hair.

It is likewise known practice to dye human keratin fibres by what is called semi-permanent coloration or direct coloration, which employs dyes that are capable of themselves providing a more or less marked modification to the natural colouring of the hair.

These direct dyes may also be used in combination with oxidizing agents, where the desire is to obtain a coloration which is lighter than the original colour of the fibres. Accordingly, these direct dyes may be used in compositions for lightening direct dyeing that are based on hydrogen peroxide and ammonia, or in compositions for oxidation dyeing in association with oxidation bases and/or couplers.

Furthermore, when a person wishes to bleach their hair, it is also known practice to carry out bleaching using lightening products based on ammonia and hydrogen peroxide.

Accordingly, it is usual to employ alkaline oxidizing compositions that are based on hydrogen peroxide and ammonia for the purpose of colouring and/or bleaching human keratin fibres, and especially the hair.

However, although these conditions of use do prove to be effective, they may give rise to a certain number of annoyances at the time of their use.

In particular, when these compositions are applied to the hair, there is generally a release of ammonia, which can lead to a suffocating odour which is irritating to the eyes, airways and mucous membranes.

Moreover, particularly in persons with a sensitive scalp, the ammonia may give rise to reactions of discomfort, such as redness, itching or pricking.

Finally, ammonia, in combination with the oxidizing agent, may also contribute to damaging the keratin fibres. Indeed, over the long term, the fibres are observed to be or more less degraded and to have a tendency to become lank, dull, fragile and difficult to style.

Accordingly, in order to remedy all of the drawbacks described above, numerous alternatives have already been proposed for the purpose of significantly reducing the levels of ammonia in compositions that are intended for the colouring and/or bleaching of fibres.

To this end, proposals have been made to apply, to the hair, colouring and/or bleaching compositions that comprise a non-volatile organic amine, such as monoethanolamine. Although such compositions do have the advantage of not releasing ammonia while they are being used, they usually give rise to reactions of discomfort, and especially to irritation in people with a sensitive scalp. Furthermore, for equivalent lightening performance, monoethanolamine damages the hair in a way which is greater than that of ammonia.

Other compositions combining ammonia with a water-soluble ammonium salt have also been envisaged. Compositions of this kind are described more particularly in patent application EP 0 148 466.

However, these compositions do not allow a satisfactory reduction in the unpleasant odours caused by the release of ammonia, and the lightening performance of this type of composition remains limited relative to that of ammonia-based compositions.

In the same way, compositions containing compounds such as ammonium, alkali metal or alkaline earth metal carbonates and hydrogen carbonates have been proposed.

Although these compositions do allow a significant reduction in the levels of ammonia, their lightening performance still remains below that of ammonia-based compositions. Moreover, these compositions continue to cause great damage to the keratin fibres.

Alternatively, compositions based on neutral or basic amino acids have been envisaged for the purpose of providing a total or partial replacement for the ammonia content.

Accordingly, patent EP 0 840 593 describes ammonia-free compositions comprising in particular, as an alkaline agent, a mixture based on a compound selected from amino acids and oligopeptides which have an amino group and a —COOH or —$SO_3$H group, and a compound selected from the group consisting of monoethanolamine, monoisopropanolamine, 2-amino-2-methylpropanol, 2-amino-2-methyl-1,3-propanediol, 2-amino-2-ethyl-1,3-propanediol and 2-amino-2-methylbutanol.

Patent applications JP 2004 262885 and JP 2004 262886 likewise describe ammonia-free compositions based on neutral or basic amino acids, non-volatile amine, and an acidic organic ammonium ion.

Finally, U.S. Pat. No. 5,131,912 describes compositions based on neutral or basic amino acids and on alkaline agents such as ammonium, alkali metal or alkaline earth metal carbonates or hydrogen carbonates. The mixture before use of these alkaline compositions with an oxidizing hydrogen peroxide composition presents a pH of between 6.5 and 7.9.

Although such compositions do have the advantage of not releasing ammonia while being used, they still do not make it possible to match the lightening performance level of the ammonia-based compositions. Furthermore, these compositions can give rise to irritation to the scalp.

The objective of the present invention is to reduce the levels of ammonia in the compositions intended, in particular, for colouring and/or for bleaching, so as to reduce the unpleasant odours accompanying the process, the irritations to the scalp and the damage to the keratin fibres, while retaining good colouring and/or bleaching properties.

This objective is achieved with the present invention, which provides a composition for treating keratin fibres, comprising, in a cosmetically acceptable medium:
- one or more alkanolamines;
- one or more amino acids; and
- one or more cationic polymers.

The composition according to the invention exhibits the advantage of minimizing, or even suppressing, the drawbacks that are caused by release of ammonia.

The composition according to the invention also allows a reduction to be achieved in the discomfort likely to be sensed at the time of application of said composition to the keratin fibres, at the scalp.

Moreover, the composition allows the damage to the fibre to be reduced, relative to conventional colouring and/or bleaching compositions containing ammonia as their primary alkaline agent.

When employed with oxidation bases and/or couplers and/or direct dyes, a colouring composition is obtained which has the further advantage of possessing good dyeing properties, and, more particularly, strong, colourful colorations which are relatively non-selective and which are highly resistant to the various forms of attack that the hair may undergo.

When the composition according to the invention is employed with an oxidizing agent, such as hydrogen peroxide, a bleaching or lightening composition is obtained which has the further advantage of leading to satisfactory lightening of the keratin fibres.

The present invention likewise provides methods of bleaching and/or colouring keratin fibres, and also provides multiple-compartment devices or kits for the implementation of these methods.

Other subjects, features, aspects and advantages of the invention will emerge more clearly from the reading of the description and the examples which follow.

In the text below, unless otherwise indicated, the end points of the ranges indicated are included in the invention.

In one particular embodiment of the invention, the alkanolamine or alkanolamines are selected from monoethanolamine, triethanolamine, monoisopropanol-amine, diisopropanolamine, N-dimethylaminoethanolamine, 2-amino-2-methyl-1-propanol, triisopropanolamine, 2-amino-2-methyl-1,3-propanediol, 3-amino-1,2-propane-diol, 3-dimethylamino-1,2-propanediol and tris-hydroxy-methy-laminomethane.

Preference is given to using monoethanolamine.

The alkanolamine or alkanolamines are generally present in the composition in accordance with the invention in an amount of between 0.1% and 15% by weight, preferably between 0.5% and 10% by weight, and more preferably between 1% and 7% by weight of the total weight of the composition.

In one particular embodiment of the invention, the amino acid or acids contain one or more amine functions and one or more acid functions. The acid function or functions may be carboxylic, sulphonic, phosphonic or phosphoric, and preferably carboxylic.

The amino acids present in the composition in accordance with the invention preferably have a molecular weight of less than 500.

In one particular embodiment of the invention, the amino acid or acids present in the composition in accordance with the present invention are α-amino acids, which is to say that they contain an amine function and a group R which are situated in the alpha position in relation to the acid function. They may, for example, be represented by the formula:

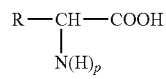

in which:

p is 1 or 2;

R represents a hydrogen atom, an aliphatic group containing or not containing a heterocyclic moiety, or an aromatic group;

where p=1, R may also form, with the nitrogen atom of —N(H)$_p$, a heterocycle. This heterocycle is preferably a saturated, 5-membered ring which is optionally substituted by one or more $C_{1-4}$ alkyl groups, or hydroxyl.

The aliphatic group is preferably a linear or branched $C_1$-$C_4$ alkyl group; a linear or branched $C_1$-$C_4$ hydroxyalkyl group; a linear or branched $C_1$-$C_{44}$ aminoalkyl group; a linear or branched $C_1$-$C_4$ ($C_1$-$C_4$ alkyl)thioalkyl group; a linear or branched $C_2$-$C_4$ carboxyalkyl group; a linear or branched ureidoalkyl group, a linear or branched guanidinoalkyl group, a linear or branched imidazoloalkyl group, or a linear or branched indoylalkyl group, the alkyl moieties of these last four groups containing one to four carbon atoms.

The aromatic group is preferably a $C_6$ aryl or $C_7$-$C_{10}$ aralkyl group, the aromatic nucleus being optionally substituted by one or more $C_1$-$C_4$ alkyl groups, or hydroxyl.

Amino acids which can be used in the present invention include, more particularly, aspartic acid, glutamic acid, alanine, arginine, aspartic acid, glutamine, glycine, histidine, isoleucine, leucine, lysine, methionine, N-phenylalanine, proline, serine, threo-nine, tryptophan, tyrosine, valine and hydroxyproline.

The amino acids that are particularly preferred in the present invention are arginine, glycine, histidine, and lysine.

The compositions employed in accordance with the invention generally have a concentration of amino acid(s) of between 0.1% and 15% by weight, preferably between 0.5% and 10% by weight, and more preferably between 1% and 10% by weight, relative to the total weight of the composition.

In one particular embodiment of the invention the alkanolamines/amino acids molar ratio is greater than or equal to 0.1, preferably greater than or equal to 1. More preferably still this ratio is greater than or equal to 1.5.

In another particular embodiment of the invention the alkanolamines/amino acids molar ratio is less than or equal to 50, preferably less than or equal to 10.

A "cationic polymer" is any polymer containing cationic groups and/or groups which can be ionized to cationic groups.

Cationic polymers include more particularly polyamine, polyaminoamide and quaternary polyammonium polymers.

The polyamine, polyaminoamide and quaternary poly-ammonium polymers that can be used in the composition of the present invention are described, in particular, in French patents FR 2 505 348 and FR 2 542 997. These polymers include the following:

(1) homopolymers or copolymers derived from esters or amides of acrylic or methacrylic acid;
(2) cationic cellulose derivatives such as:
   (a) the cellulose ether derivatives containing quaternary ammonium groups that are described in French patent FR 1 492 597;
   (b) the copolymers of cellulose or cellulose derivatives grafted with a water-soluble quaternary ammonium monomer, which are described in particular in U.S. Pat. No. 4,131,576, such as hydroxyalkylcelluloses, for instance hydroxymethyl-, hydroxyethyl- or hydroxypropyl celluloses grafted in particular with a methacryloylethyltrimethyl-ammonium, methacrylamidopropyltrimethyl-ammonium or dimethyldiallylammonium salt; an example that may be mentioned is polyquaternium 10 (INCI name);
(3) the other cationic polysaccharides described more particularly in U.S. Pat. No. 3,589,578 and U.S. Pat. No. 4,031,307, such as guar gums containing cationic trialkylammonium groups;
(4) polymers composed of piperazinyl units and divalent alkylene or hydroxyalkylene groups having straight or branched chains which are optionally interrupted by oxygen, sulphur or nitrogen atoms or by aromatic or heterocyclic rings, and also the oxidation and/or quaternization products of these polymers. Polymers of this kind are described in particular in French patents FR 2 162 025 and FR 2 280 361;
(5) polyaminoamides which are soluble in water, such as those, in particular, described in French patents FR 2 252 840 and FR 2 368 508;
(6) polyaminoamide derivatives, for example, the adipic acid/dialkylaminohydroxyalkyldialkylene-triamine polymers in which the alkyl group contains 1 to 4 carbon atoms and is preferably a methyl, ethyl or propyl group, and the alkylene group contains 1 to 4 carbon atoms and is preferably the ethylene group. Polymers of this kind are described in particular in French patent FR 1 583 363;
(7) polymers obtained by reacting a polyalkylene-poly-amine containing two primary amine groups and at least one secondary amine group with a dicarboxylic acid selected from diglycolic acid and saturated aliphatic dicarboxylic acids having 3 to 8 carbon atoms. The molar ratio of the polyalkylene-polyamine to the dicarboxylic acid is between 0.8:1 and 1.4:1, and the resulting polyaminoamide is reacted with epichlorohydrin in a molar ratio of epichlorohydrin to the secondary amine group of the polyaminoamide of between 0.5:1 and 1.8:1. Polymers of this kind are described in particular in U.S. Pat. No. 3,227,615 and U.S. Pat. No. 2,961,347;
(8) alkyldiallylamine or dialkyldiallylammonium cyclopolymers such as the homopolymer of dimethyl-diallylammonium chloride, and the copolymers of diallyldimethylammonium chloride and acrylamide;
(9) quaternary diammonium polymers having a number-average molecular mass of generally between 1000 and 100 000, such as those described, for example, in French patents FR 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020; an example that may be mentioned is hexadimethrine chloride (INCI name), sold by Chimex under the name Mexomere PO;
(10) quaternary polyammonium polymers such as those, in particular, described in patent application EP-A-122 324;
(11) quaternary vinylpyrrolidone and vinylimidazole polymers such as, for example, the products sold under the names Luviquat® FC 905, FC 550 and FC 370 by BASF;
(12) polyamines such as Polyquart® H sold by Henkel, listed under the name "POLYETHYLENE GLYCOL (15) TALLOW POLYAMINE" in the CTFA dictionary;
(13) crosslinked polymers of methacryloyloxyalkyl($C_1$-$C_4$) trialkyl($C_1$-$C_4$) ammonium salts, such as those sold under the name Salcare® SC 92, Salcare® SC 95 and Salcare® SC 96 by Allied Colloids; and mixtures thereof.

Other cationic polymers which can be used in the context of the invention are cationic proteins or hydrolysates of cationic proteins, polyalkyleneimines, especially polyethyleneimines, polymers containing vinylpyridine or vinylpyridinium units, condensates of polyamines and epichlorohydrin, quaternary polyureylenes and chitin derivatives.

The cationic polymers are preferably selected from polymers as defined in points (8) and (9), and especially hexadimethrine chloride and the homopolymers or copolymers of dimethyldiallylammonium chloride. More preferably still, the cationic polymer is hexadimethrine chloride.

The cationic polymer or polymers represent generally from 0.01% to 40%, preferably from 0.1% to 20%, by weight, relative to the total weight of the composition according to the invention.

In one particular embodiment the composition in accordance with the invention comprises monoethanolamine, arginine and hexadimethrine chloride.

In another particular embodiment the composition in accordance with the invention comprises monoethanolamine, lysine and hexadimethrine chloride.

In another particular embodiment the composition in accordance with the invention comprises 2-methyl-2-aminopropan-1-ol, arginine and hexadimethrine chloride.

In another particular embodiment the composition in accordance with the invention comprises monoethanolamine, hystidine and hexadimethrine chloride.

The composition in accordance with the invention may comprise one or more additional alkaline agents.

In one particular embodiment of the invention, the additional alkaline agent or agents are selected from alkali metal or alkaline earth metal silicates.

The alkali metals or alkaline earth metals may be selected from lithium, sodium, potassium, magnesium, calcium and barium.

The additional alkaline agent is preferably sodium metasilicate.

The composition in accordance with the invention preferably does not contain ammonia.

When present, the additional alkaline agent or agents represent preferably from 0.1% to 5% by weight, approximately, of the total weight of the colouring composition, and more preferably from 0.1% to 3% by weight, approximately.

In one particular embodiment of the invention the composition comprises monoethanolamine, one or more amino acids, one or more cationic polymers and sodium metasilicate.

In one particular embodiment the composition in accordance with the invention comprises monoethanol-amine, lysine, hexadimethrine chloride and sodium metasilicate.

In one particular embodiment the composition in accordance with the invention comprises monoethanol-amine, arginine, hexadimethrine chloride and sodium metasilicate.

The composition in accordance with the invention may comprise one or more oxidizing agents selected, for example, from hydrogen peroxide, urea peroxide, alkali metal bromates, persalts such as perborates and persulphates, and enzymes such as peroxidases and two electron or four electron oxidoreductases. The use of hydrogen peroxide is particularly preferred.

The oxidizing agent content of the composition may be between 0.1% and 10% by weight of the composition, preferably between 0.5% and 6% by weight of the composition.

The pH of the composition after mixing with the oxidizing agent or agents is generally between 5.5 and 10.5, preferably between 6 and 10.

The dye composition in accordance with the invention may also comprise various adjuvants which are commonly used in hair treatment compositions, such as anionic, cationic, non-ionic, amphoteric and zwitterionic surfactants or mixtures thereof, anionic, non-ionic, amphoteric and zwitterionic polymers or mixtures thereof, organic or inorganic thickeners, and especially anionic, cationic, nonionic and amphoteric polymeric associative thickeners, reducing agents or antioxidants other than the dithionites, and also penetrants, sequestrants, perfumes, buffers, dispersants, conditioning agents such as, for example, modified or unmodified, volatile or non-volatile silicones, and also film formers, ceramides, preservatives and opacifiers.

The above adjuvants are generally present in an amount in each case of between 0.01% and 20% by weight, relative to the weight of the composition.

A cosmetically acceptable medium for the purposes of the present invention is a medium which is compatible with the keratin fibres, and more particularly the hair.

The medium appropriate for the composition according to the invention is a cosmetically acceptable medium which generally comprises water or a mixture of water and one or more organic solvents. Organic solvents include, for example, the $C_1$-$C_4$ lower alkanols, such as ethanol and isopropanol; polyols and polyol ethers such as 2-butoxyethanol, propylene glycol, glycerol, propylene glycol monomethyl ether, diethylene glycol monoethyl and monomethyl ether, and also aromatic alcohols such as benzyl alcohol or phenoxyethanol, and mixtures thereof.

The solvents are preferably present in proportions of between 1% and 40% by weight, approximately, relative to the total weight of the cosmetic composition, and more preferably between 5% and 30% by weight, approximately.

The person skilled in the art will of course ensure that this or these optional complementary compounds are chosen such that the advantageous properties intrinsically attached to the composition in accordance with the invention are not, or not substantially, adversely affected by the intended addition or additions.

The composition according to the invention may take various forms, such as the form of liquids, creams, gels, or any other form appropriate for colouring and/or bleaching keratin fibres, and especially human keratin fibres such as the hair.

The composition according to the invention may further comprise one or more oxidation bases and/or one or more couplers and/or one or more direct dyes.

When the composition according to the invention comprises one or more oxidation bases and/or one or more couplers and/or one or more direct dyes, said composition is then a colouring composition.

When the colouring composition comprises, as dye, one or more oxidation bases optionally in combination with one or more couplers, said composition is then an oxidation colouring composition.

The oxidation base or bases are selected from oxidation bases which are conventionally used for oxidation colouring. As examples, the oxidation bases may be selected from para-phenylenediamines, bisphenylalkylenediamines, para-aminophenols, ortho-aminophenols and heterocyclic bases and their addition salts with an acid or with an alkaline agent.

The para-phenylenediamines include more particularly, by way of example, para-phenylenediamine, para-toluoylenediamine, 2-chloro-paraphenylenediamine, 2,3-dimethyl-para-phenylenediamine, 2,6-dimethyl-para-phenylenediamine, 2,6-diethyl-para-phenylenediamine, 2,5-dimethyl-para-phenylene diamine, N,N-dimethyl-para-phenylenediamine, N,N-diethyl-para-phenylenediamine, N,N-dipropyl-paraphenylenediamine, 4-amino-N,N-diethyl-3-methylaniline, N,N-bis(β-hydroxyethyl)-para-phenylenediamine, 4-N,N-bis(βhydroxyethyl)amino 2- methylaniline, 4-N,N-bis(βhydroxyethyl)amino 2-chloro-aniline, 2-β-hydroxyethyl-para-phenylenediamine, 2-fluoro-para-phenylenediamine, 2-isopropyl-para-phenylenediamine, N-(β- hydroxy-propyl)-para-phenylene-diamine, 2-hydroxymethyl-para-phenylenediamine, N,N-dimethyl-3- methylpara-phenylenediamine, N,N-(ethyl-β-hydroxyethyl)-para-phenylenediamine, N-(β,γ-dihydroxy-propyl)-para-phenylenediamine, N-(4'- aminophen-yl)-para-phenylenediamine, N-phenyl-para-phenylene-diamine, 2-β-hydroxyethyloxypara- phenylenediamine, 2-β-acetylaminoethyloxy-para-phenylenediamine, N-(β- methoxyethyl)-para-phenylenediamine and 4'-amino- phenyl-1-(3hydroxy)pyrrolidine, and their addition salts with an acid or with an alkaline agent.

Of the abovementioned para-phenylenediamines, particular preference is given to para-phenylene-diamine, para-toluoylenediamine, 2-isopropyl-para-phenylenediamine, 2-β-hydroxyethyl-paraphenylene- diamine, 2-β-hydroxyethyloxy-para-phenylenediamine, 2,6-dimethyl-para-phenylenediamine, 2,6- diethyl-para-phenylenediamine, 2,3-dimethylparaphenylenediamine, N,N-bis(βhydroxyethyl)- paraphenylenediamine, 2-chloro-para-phenylenediamine, 2-β- acetylaminoethyloxypara-phenylenediamine, and their addition salts with an acid or with an alkaline agent.

The bis phenylalkylenediamines include more particularly, by way of example, N,N'-bis (β-hydroxyethyl)-N,N'-bis(4'-aminophenyl)-1,3- diamino-propanol, N,N'-bis(βhydroxyethyl)-N,N'-bis(4'-amino-phenyl) ethylenediamine, N,N'-bis (4-aminophenyl)tetra-methylenediamine, N,N'- bis (βhydroxyethyl)- N,N'-bis (4-aminophenyl) tetramethylenediamine, N,N'-bis(4-methylaminophenyl) tetramethylenediamine, N,N'-bis (ethyl)-N,N'-bis(4'-amino-3'-methylphenyl) ethylene- diamine, 1,8-bis(2,5-diaminophenoxy)-3,5-dioxaoctane, and their addition salts with an acid or with an alkaline agent.

The para-aminophenols include more particularly, by way of example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-β-hydroxyethylaminomethyl)phenol, 4-amino-2-fluorophenol, and their addition salts with an acid or with an alkaline agent.

The ortho-aminophenols include more particularly, by way of example, 2-aminophenol, 2-amino-5-methylphenol, 2-amino-6-methylphenol, 5-acetamido-2-aminophenol, and their addition salts with an acid or with an alkaline agent.

The heterocyclic bases include more particularly, by way of example, pyridine derivatives, pyrimidine derivatives and pyrazole derivatives and their addition salts with an acid or with an alkaline agent. Mention may be made particularly of 1-β-hydroxyethyl-4,5-diaminopyrazole, 2,3-diamino-6,7-dihydro-1H,5H-pyrazolo[1,2-a]pyrazol-1-one and their salts.

When used, the oxidation base or bases represent preferably from 0.005% to 15% by weight, and more preferably from 0.01% to 10% by weight, relative to the total weight of the composition.

The coupler or couplers are selected from couplers conventionally used for oxidation colouring. As examples, the coupler or couplers are selected from couplers which are customarily used for the dyeing of keratin fibres. Of these couplers, mention may be made in particular of meta-phenylenediamines, meta-aminophenols, meta-diphenols, naphthalenic couplers, heterocyclic couplers and their addition salts with an acid or with an alkaline agent.

These couplers are selected more particularly from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxy-benzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl-pyrazolo[3,2-c]-1,2,4-triazole, 6-methylpyrazolo[1,5-a]-benzimidazole, and their addition salts with an acid or with an alkaline agent.

When present, the coupler or couplers represent preferably from 0.001% to 15% by weight, and more preferably from 0.05% to 10% by weight, relative to the total weight of the composition.

Generally speaking, the addition salts of the oxidation bases and of the couplers which can be used in the context of the invention are selected in particular from addition salts with an acid, such as hydrochlorides, hydrobromides, sulphates, citrates, succinates, tartrates, tosylates, benzenesulphonates, phosphates and acetates, and addition salts with a base such as sodium hydroxide, potassium hydroxide, ammonia, amines or alkanolamines.

When the colouring composition contains neither oxidation bases nor couplers but does contain direct dyes, said composition is an optionally lightening direct colouring composition.

The direct dye or dyes which can be used in the colouring composition may be selected from neutral, acidic or cationic nitro dyes of the benzene series, neutral, acidic or cationic direct azo dyes, neutral, acidic or cationic direct quinone— and especially anthraquinone—dyes, direct azine dyes, direct triarylmethane dyes, direct indoamine dyes and direct natural dyes, alone or in a mixture.

The direct nitrobenzene dyes which can be used according to the invention include, without limitation, the following compounds:
1,4-diamino-2-nitrobenzene,
1-amino-2-nitro-4-β-hydroxyethylaminobenzene
1-amino-2-nitro-4-bis(βhydroxyethyl)-aminobenzene
1,4-bis(β-hydroxyethylamino)-2-nitrobenzene
1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris-(hydroxymethyl)-methylamino-5-nitrobenzene
1-hydroxy-2-amino-5-nitrobenzene
1-hydroxy-2-amino-4-nitrobenzene
1-hydroxy-3-nitro-4-aminobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β,γ-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)-amino-3-nitrobenzene
1-β-hydroxyethylamino-2-nitrobenzene
1-hydroxy-4-β-hydroxyethylamino-3-nitrobenzene.

The direct azo dyes which can be used according to the invention include the cationic azo dyes described in patent applications WO 95/15144, WO 95/01772, EP 714954, FR 2 822 696, FR 2 825 702, FR 2 825 625, FR 2 822 698, FR 2 822 693, FR 2 822 694, FR 2 829 926, FR 2 807 652, WO 02/078660, WO 02/100834, WO 02/100369 and FR 2 844 269.

Of these compounds, mention may be made particularly of the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]-pyridinium methyl sulphate.

Mention may also be made, among the direct azo dyes, of the following dyes, which are described in the third edition of the Colour Index International:
Acid Yellow 9
Acid Black 1
Basic Red 22
Basic Red 76
Basic Yellow 57
Basic Brown 16
Acid Yellow 36
Acid Orange 7
Acid Red 33
Acid Red 35
Basic Brown 17
Acid Yellow 23
Acid Orange 24.

Mention may also be made of 1-(4'-aminodiphenylazo)-2-methyl-4-bis(βhydroxyethyl)aminobenzene and of 4-hydroxy-3-(2-methoxyphenylazo)-1-naphthalenesulphonic acid.

Of the direct quinone dyes, mention may be made of the following dyes:
Acid Violet 43
Acid Blue 62
Basic Blue 22
Basic Blue 99 and also of the following compounds:
1-N-methylmorpholiniopropylamino-4-hydroxy-anthraquinone 1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Of the azine dyes, mention may be made of the following compounds:

Basic Blue 17
Basic Red 2.

Of the triarylmethane dyes which can be used according to the invention, mention may be made of the following compounds:

Basic Green 1
Acid Blue 9
Basic Violet 3
Basic Violet 14
Basic Blue 7
Acid Violet 49
Basic Blue 26
Acid Blue 7.

Of the indoamine dyes which can be used according to the invention, mention may be made of the following compound:

2-β-hydroxyethylamino-5-[bis(β-4'-hydroxyethyl)amino]anilino-1,4-benzoquinone.

Among the natural direct dyes which can be used according to the invention, mention may be made of carminic acid, kermesic acid, purpurogallin, protocatechaldehyde, isatin, curcumin, spinulosin and apigenidin, and the orceins. Use may also be made of extracts or decoctions which contain these natural dyes, and especially the henna-based poultices or extracts.

The direct dye or dyes represent preferably from 0.001% to 20% by weight, approximately, of the total weight of the colouring composition, and more preferably from 0.005 to 10% by weight, approximately.

When the composition according to the invention contains no dye but does contain one or more oxidizing agents, said composition is then a composition for bleaching keratin fibres.

Bleaching for the purposes of the present invention means the total or partial destruction of the natural pigments present in the keratin fibres (in particular, eumelanins and phaeomelanins).

The present invention also provides a method of oxidation-colouring keratin fibres, and especially human keratin fibres such as the hair, which involves applying to said fibres a colouring composition as defined above, comprising, as dye(s), one or more oxidation bases, optionally in combination with one or more couplers and/or one or more direct dyes, in the presence of one or more oxidizing agents, for a time sufficient to develop the desired coloration.

After a leave-on time of 5 minutes to 1 hour, preferably of 10 minutes to 1 hour approximately, the keratin fibres are rinsed, washed with shampoo, rinsed again and then dried.

The oxidizing agent may be added to the colouring composition at the exact time of use, or it may be employed on the basis of an oxidizing composition containing it, which is applied simultaneously or sequentially to the colouring composition.

In one embodiment the present invention further provides a method of directly colouring, with optional lightening—keratin fibres, and especially human keratin fibres such as the hair, which involves applying to said fibres a colouring composition as defined above, comprising, as dye(s), one or more direct dyes, optionally in the presence of one or more oxidizing agents, for a time sufficient to give the desired coloration and, optionally, the desired lightening.

The present invention likewise provides a method of bleaching keratin fibres, and especially human keratin fibres such as the hair, which involves applying to said fibres a composition comprising one or more alkanolamines, one or more amino acids and one or more cationic polymers in the presence of one or more oxidizing agents, leaving the composition to act for a leave-on time which is sufficient to give the required bleaching, removing the composition by rinsing with water, followed by washing with a shampoo and then, where appropriate, by drying.

The leave-on time ranges between 5 minutes and 1 hour approximately, more preferably between 10 minutes and 1 hour approximately.

Further provided by the invention is a multiple-compartment device for the dyeing or bleaching of keratin fibres, especially human keratin fibres. A first compartment contains a composition comprising one or more alkanolamines, one or more amino acids, one or more cationic polymers and, where appropriate, one or more oxidation bases and/or one or more couplers and/or one or more direct dyes, and a second compartment, containing an oxidizing composition comprising one or more oxidizing agents.

The examples which follow illustrate the invention, without having any limitative character.

EXAMPLES

In the table below, a.s. signifies active substance.

| | Amount (g %) | | | | | | |
|---|---|---|---|---|---|---|---|
| | A | B | C | D | E | F | G |
| Lauric acid | 3 | 3 | 3 | 3 | 3 | 3 | 3 |
| Glycol distearate | 2 | 2 | 2 | 2 | 2 | 2 | 2 |
| Cetylstearyl alcohol (C16/C18 50/50) | 11.5 | 11.5 | 11.5 | 11.5 | 11.5 | 11.5 | 11.5 |
| Ethoxylated lauryl alcohol (12EO) | 7 | 7 | 7 | 7 | 7 | 7 | 7 |
| Ethoxylated oleocetyl alcohol (30EO) | 4 | 4 | 4 | 4 | 4 | 4 | 4 |
| Ethoxylated decyl alcohol (3EO) | 10 | 10 | 10 | 10 | 10 | 10 | 10 |
| Carbomer | 0.4 | 0.4 | 0.4 | 0.4 | 0.4 | 0.4 | 0.4 |
| Silica | 1.2 | 1.2 | 1.2 | 1.2 | 1.2 | 1.2 | 1.2 |
| Propylene glycol | 10 | 10 | 10 | 10 | 10 | 10 | 10 |
| Hexadimethrine chloride, 60% in aqueous solution | 4 (2.4 a.s.) | 2 (1.2 a.s.) | 4 (2.4 a.s.) | 2 (1.2 a.s.) | 4 (2.4 a.s.) | 4 (2.4 a.s.) | 4 (2.4 a.s.) |

-continued

| | Amount (g %) | | | | | | |
|---|---|---|---|---|---|---|---|
| | A | B | C | D | E | F | G |
| Dimethyldiallylammonium chloride/acrylic acid (80/20) copolymer in aqueous solution at 40.5% (Polyquaternium-22) | / | 2 (0.81 a.s.) | / | 5 (2.025 a.s.) | / | / | 3 (1.215 a.s.) |
| DTPA (diethylene-triaminepentaacetic acid, pentasodium salt) 40% in aqueous solution | 2 (0.8 a.s.) | 2 (0.8 a.s.) | 2 (0.8 a.s.) | 2 (0.8 a.s.) | 2 (0.8 a.s.) | 2 (0.8 a.s.) | 2 (0.8 a.s.) |
| Sodium metabisulphite | 0.7 | 0.7 | 0.7 | 0.7 | 0.7 | 0.7 | 0.7 |
| Erythorbic acid | 0.3 | 0.3 | 0.3 | 0.3 | 0.3 | 0.3 | 0.3 |
| Monoethanolamine | 6.2 | / | 6.2 | 5.4 | 4.5 | 4.2 | 6.2 |
| 2-Amino-2-methyl propan-1-ol | / | 1 | / | / | / | / | / |
| ARGININE | 5 | 6 | 4 | / | / | / | / |
| LYSINE | / | / | / | 5 | 4 | 5 | / |
| HYSTIDINE | / | / | / | / | / | / | 4 |
| Sodium metasilicate | / | / | 1.5 | / | 1 | 2 | / |
| Para-phenylenediamine | / | 0.51 | / | 0.3 | 1 | / | 1 |
| 4-Methylaminophenol hemisulphate | / | 0.085 | / | 0.063 | 0.16 | / | 0.16 |
| 1,3-Dihydroxybenzene | / | 0.38 | / | 0.24 | 0.75 | / | 0.75 |
| 1-Hydroxy-3-amino-benzene | / | 0.11 | / | 0.08 | 0.21 | / | 0.21 |
| 1-(β-Hydroxyethyloxy)-2,4-diaminobenzene dihydrochloride | / | 0.025 | / | 0.005 | 0.052 | / | 0.052 |
| 1-Methyl-2-hydroxy-4-(β-hydroxyethylamino)-benzene | / | 0.25 | / | 0.097 | 0.49 | / | 0.49 |
| 1-Hydroxy-4-amino-benzene | 0.545 | 0.23 | 0.545 | 0.17 | 0.44 | 0.545 | 0.44 |
| 1-Methyl-2-hydroxy-4-aminobenzene | 0.615 | 0.05 | 0.615 | 0.057 | 0.1 | 0.615 | 0.1 |
| Perfume | 0.75 | 0.75 | 0.75 | 0.75 | 0.75 | 0.75 | 0.75 |
| Deionized water | qs 100 | qs 100 | qs 100 | qs 100 | qs 100 | qs 100 | qs 100 |

Colouring compositions A, B, C, D, E, F and G are mixed, at the time of use, in a plastic bowl and for 2 minutes with an aqueous oxidizing composition containing 6% hydrogen peroxide and having a pH of 2.3, in a proportion of 1 part by weight of colouring composition to 1.5 parts by weight of oxidizing composition.

The resulting mixtures do not have unpleasant odours. They are applied for 30 minutes at ambient temperature to brown hair.

After rinsing and drying, the hair is dyed uniformly.

The invention claimed is:

1. A cosmetic composition comprising, in a cosmetically acceptable medium:
   at least one alkanolamine,
   at least one amino acid, and
   at least one cationic polymer,
   wherein the molar ratio of the at least one alkanolamine to the at least one amino acid is less than or equal to 10.

2. The cosmetic composition according to claim 1, wherein the at least one alkanolamine is chosen from monoethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, and tris-hydroxymethylaminomethane.

3. The cosmetic composition according to claim 2, wherein the alkanolamine is monoethanolamine.

4. The cosmetic composition according to claim 1, wherein the at least one amino acid is chosen from the compounds of formula:

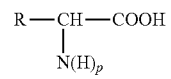

wherein
p is 1 or 2,
R is chosen from a hydrogen atom, and aliphatic groups optionally comprising groups chosen from heterocyclic and aromatic groups, and
when p=1, R may also form, with the nitrogen atom of —N(H)$_p$, a heterocycle.

5. The cosmetic composition according to claim 4, wherein the at least one amino acid is chosen from arginine, glycine, histidine, and lysine.

6. The cosmetic composition according to claim 1, wherein the at least one cationic polymer is chosen from polyamine, polyaminoamide, and quaternary polyammonium polymers.

7. The cosmetic composition according to claim 6, wherein the cationic polymer is hexadimethrine chloride.

8. The cosmetic composition according to claim 1, further comprising at least one oxidation base.

9. The cosmetic composition according to claim 1, further comprising at least one coupler.

10. The cosmetic composition according to claim 1, further comprising at least one direct dye.

11. The cosmetic composition according to claim 1, further comprising at least one oxidizing agent.

12. A method for oxidation-coloring keratin fibers, comprising applying to keratin fibers in the presence of at least one oxidizing agent, for a time sufficient to develop the desired color, a composition comprising in a cosmetically acceptable medium:
- at least one alkanolamine,
- at least one amino acid,
- at least one cationic polymer, and
- at least one oxidation base,
- wherein the molar ratio of the at least one alkanolamine to the at least one amino acid is less than or equal to 10.

13. The method for oxidation-coloring keratin fibers according to claim 12, wherein the composition further comprises at least one coupler.

14. The method for oxidation-coloring keratin fibers according to claim 12, wherein the composition further comprises at least one direct dye.

15. A method for direct dye coloring of keratin fibers, comprising applying to keratin fibers for a time sufficient to give the desired color, a composition comprising in a cosmetically acceptable medium:
- at least one alkanolamine,
- at least one amino acid,
- at least one cationic polymer, and
- at least one direct dye, wherein the molar ratio of the at least one alkanolamine to the at least one amino acid is less than or equal to 10.

16. The method for direct dye coloring keratin fibers according to claim 15, wherein the composition further comprises at least one oxidizing agent.

17. The method for direct dye coloring keratin fibers according to claim 15, wherein the method further comprises lightening the keratin fibers.

18. A method for bleaching keratin fibers comprising applying to keratin fibers in the presence of at least one oxidizing agent, for a time sufficient to give the desired bleaching, a composition comprising in a cosmetically acceptable medium:
- at least one alkanolamine,
- at least one amino acid, and
- at least one cationic polymer,
- wherein the molar ratio of the at least one alkanolamine to the at least one amino acid is less than or equal to 10.

19. A multiple-compartment device for the dyeing of keratin fibers, comprising in a first compartment comprising in a first compartment comprising a composition comprising, in a cosmetically acceptable medium:
- at least one alkanolamine,
- at least one amino acid,
- at least one cationic polymer, and
- at least one oxidation base,
- wherein the molar ratio of the at least one alkanolamine to the at least one amino acid is less than or equal to 10, and
a second compartment comprising an oxidizing composition comprising at least one oxidizing agent.

20. The multiple-compartment device according to claim 19, wherein the composition in the first compartment further comprises at least one coupler.

21. The multiple-compartment device according to claim 19, wherein the composition in the first compartment comprises at least one direct dye.

22. A multiple-compartment device for the bleaching of keratin fibers, comprising in a first compartment comprising a composition comprising, in a cosmetically acceptable medium:
- at least one alkanolamine,
- at least one amino acid, and
- at least one cationic polymer, wherein the molar ratio of the at least one alkanolamine to the at least one amino acid is less than or equal to 10, and a second compartment containing an oxidizing composition comprising at least one oxidizing agent.

* * * * *